United States Patent [19]

Kimura

[11] Patent Number: 4,797,664

[45] Date of Patent: Jan. 10, 1989

[54] ENVIRNMENTAL ABNORMALITY DETECTION APPARATUS

[75] Inventor: Tatsuo Kimura, Tokyo, Japan

[73] Assignee: Nittan Company, Limited, Tokyo, Japan

[21] Appl. No.: 95,885

[22] Filed: Sep. 14, 1987

[30] Foreign Application Priority Data

Sep. 29, 1986 [JP] Japan ................................ 61-228389

[51] Int. Cl.$^4$ .......................... G08B 23/00; G05B 9/02
[52] U.S. Cl. .................................... 340/693; 340/584; 364/184
[58] Field of Search ................ 340/693, 333, 628–630, 340/584, 586; 364/184–187

[56] References Cited

U.S. PATENT DOCUMENTS 4,491,830  1/1985  Miyabe ................................ 340/584
4,673,928  6/1987  Guim ............................... 340/693 X
4,734,694  3/1988  Umetsu et al. ................. 340/825.44

Primary Examiner—Glen R. Swann
Assistant Examiner—Thomas J. Mullen, Jr.
Attorney, Agent, or Firm—Hill, Van Santen, Steadman & Simpson

[57] ABSTRACT

An environmental abnormality detection apparatus has a detection portion for detecting a phenomenon such as a fire or gas leakage, and a signal processor such as a microcomputer or the like for determining whether an environmental abnormality has occurred in accordance with a detection signal from the detection portion and for generating an alarm signal when the abnormality occurs. A power source control circuit is provided to intermittently supply power to the signal processor and to stop power supply in accordance with an end of processing signal from the signal processor.

4 Claims, 2 Drawing Sheets

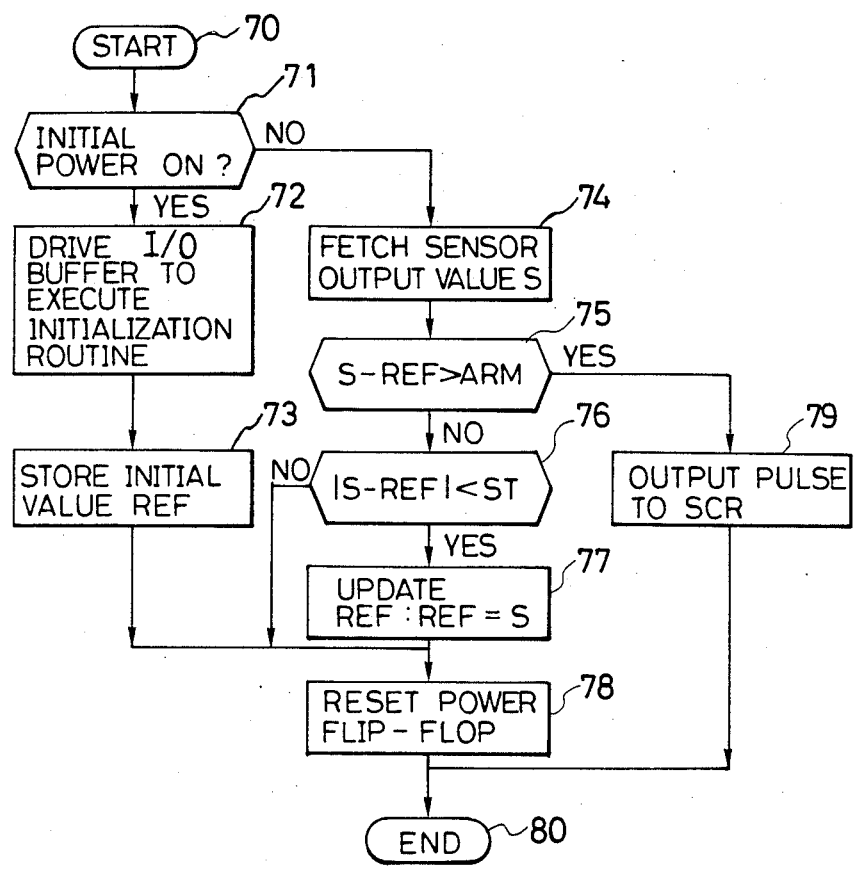

ENVIRNMENTAL ABNORMALITY DETECTION APPARATUS

BACKGROUND OF THE INVENTION

The present invention relates to an environmental abnormality detection apparatus used in an alarm device for a fire, gas leakage, or the like.

A conventional fire detector using a microcomputer in a signal processor for improving reliability is disclosed in Japanese Patent Disclosure (Kokai) No. 60-164896. In addition, a fire alarm device constituted by a receiver and a plurality of fire detectors is designed to minimize a monitoring current of each fire detector so as to reduce entire power consumption.

When a microcomputer is used in an environmental abnormality detection apparatus such as a fire detector, a highly reliable device, suitable to a place where alarm errors are not so often generated, can be provided. However, a microcomputer requires large power consumption regardless of whether it executes processing or not. Even a microcomputer using a CMOS requires several mA which is several hundreds times that of a conventional fire detector.

SUMMARY OF THE INVENTION

It is, therefore, an object of the present invention to provide an environmental abnormality detection apparatus wherein monitoring current consumption is minimized.

It is another object of the present invention to provide an environmental abnormality detection apparatus wherein optimum conditions can be set and variations in detection are less.

In order to achieve the above objects, there is provided an environmental abnormality detection apparatus having a detection portion for detecting a phenomenon such as a fire or gas leakage, a signal processor constituted by a microcomputer or the like for determining whether an environmental abnormality has occurred in accordance with a detection signal from the detection portion and for generating an alarm signal when the abnormality occurs, and a power source control circuit to intermittently supply power to the signal processor and to stop power supply in accordance with an end of processing signal from the signal processor.

BRIEF DESCRIPTION OF THE DRAWINGS

FIG. 3 is a flow chart of the detector in FIG. 1.

DETAILED DESCRIPTION OF THE PREFERRED EMBODIMENT

An environmental abnormality detection apparatus of the present invention will now be described in detail with reference to the accompanying drawings.

Figure 1:
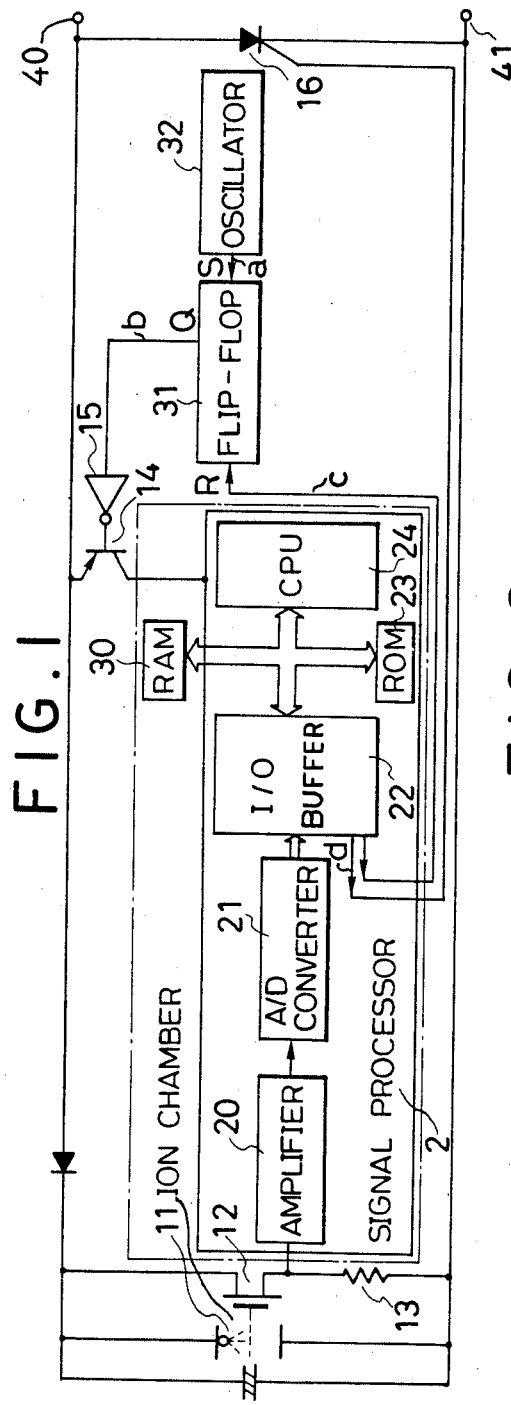
FIG. 1 is a block diagram of an embodiment of an environmental abnormality detection apparatus of the present invention.

FIG. 1 is a block diagram of an embodiment of the environmental abnormality detection apparatus of the present invention. The environmental abnormality detection apparatus shown in FIG. 1 is an ionization smoke detector, terminals 40 and 41 of which are connected to a pair of transmission lines extending from a central monitor device (not shown). This ionization smoke detector includes a detection portion consisting of an ion chamber 11 which is ionized by a radiation source, a field effect transistor 12 for converting an impedance of an intermediate electrode of the ion chamber 11, and a resistor 13 for extracting an output from the field effect transistor 12; a signal processor consisting of an amplifier 20, an A/D converter 21, an I/O port 22, a RAM (Random Access Memory) 30, a ROM (Read Only Memory) 23, and a CPU 24; a power control circuit consisting of a transistor 14, an inverter 15, a flip-flop 31, and an oscillator 32; and an SCR 16 for short-circuiting a pair of transmission lines with a low impedance upon operation. The oscillator 32, the flip-flop 31, the inverter 15, and the ROM 30 are always supplied with power through a stabilized power source circuit (not shown).

Figure 2:
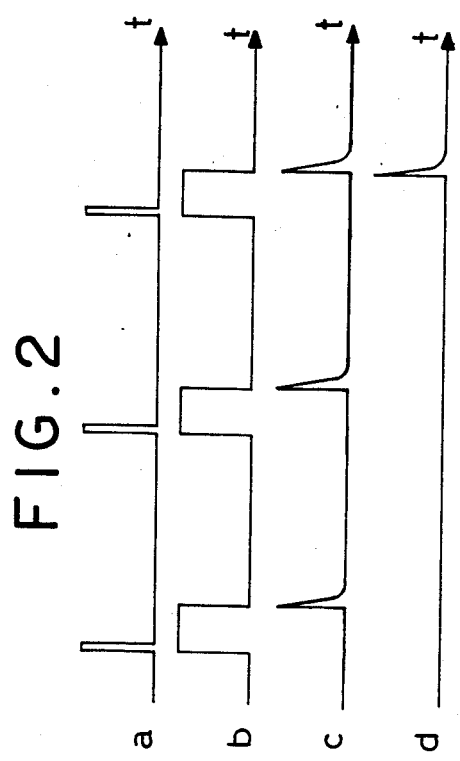
FIG. 2 is a timing chart for explaining an operation of the detector in FIG. 1.

An operation of the ionization smoke detector having the above arrangement will be described below with reference to the timing chart shown in FIG. 2. The oscillator 32 always outputs a pulse signal a of a predetermined cycle as shown in FIG. 2. The pulse signal a is input to a set terminal S of the flip-flop 31. When the flip-flop 31 is set, it sets a Q output b at a high level. Therefore, an output from the inverter 15 goes to a low level to cause a predetermined current to flow to the base of the transistor 14 so as to turn it on. At this time, power is supplied to the signal processor 2 through the transistor 14. When the CPU 24 of the signal processor 2 is supplied with power, it begins to execute programs stored in the ROM 23 from the beginning. Additionally, a voltage proportional to the smoke concentration detected in the ion chamber 11 is supplied across both the ends of the resistor 13. The smoke detection operation in the ion chamber 11 is the same as that of a conventional ionization smoke detector, and a detailed description thereof is not necessary. This detection voltage is amplified to be a predetermined level by the amplifier 20, A/D-converted by the A/D converter 21, and supplied to the I/O buffer 22. The CPU 24 determines whether an abnormality (fire) has occurred in accordance with past data stored in the RAM 30 and currently fetched data (smoke concentration). If the CPU 24 determines that no abnormality has occurred, it generates an end of processing signal c at the reset terminal R ofthe flip-flop 31 through the I/O buffer 22. When the flip-flop 31 is reset, it sets the Q output b at a low level. An output from the inverter 15 goes to a high level to turn off the transistor 14, so that the signal processor 2 is no longer supplied with power. A pulse is supplied from the oscillator 32 again after a predetermined time, and the signal processor 2 is supplied with power to execute a monitoring operation. Thus, the monitoring operation is executed every few seconds in a normal monitoring state. If the signal processor 2 determines that an environmental abnormality has occurred, an alarm signal d is supplied from the I/O buffer 22. The alarm signal d is supplied to the gate of the SCR 16 to trigger it. Terminals 40 and 41 are then connected with a low impedance, so that an operation state of the detector can be supplied as an output to the outside.

When the CPU determines whether an environmental abnormality has occurred, processing of higher complexity requires more information such as past data (history data) and a time interval. When history data must be maintained, the RAM 30 must be continuously supplied with power. However, when history data is unnecessary, the RAM 30 need only be applied with power when the CPU 24 operates.

A fire alarm device can generally monitor a fire if a monitoring operation is executed every few seconds. In addition, if signal processing is executed by a microcomputer, the processing time becomes very short although it differs case by case, and power supply is stopped at the same time the signal processing is completed, resulting in efficient saving of energy.

An example of a program of the signal processing will now be described below with reference to the flow chart shown in FIG. 3. In step 70, a power source is turned on. In step 71, the CPU determines whether the power on is an initial power on in accordance with the presence or absence of a password which is registered in the RAM. If YES in step 71, the flow advances to step 72, and if NO in step 71, the flow advances to step 74. In step 72, the buffer (and other components as may be needed) are driven to execute the initialization routine. At the same time, the password is registered. In step 73, a sensor (smoke detection) output value S is fetched and an initial value REF is stored in the buffer. Then, the flow advances to step 78. In step 74, the sensor output value S is fetched. In step 75, the CPU determines whether the sensor output value S is larger than a predetermined alarm value ARM as compared with the initial value REF. If YES in step 75, the flow advances to step 79, and if NO in step 75, the flow advances to step 76. In step 79, a pulse (alarm signal) is output to the SCR to trigger it. In step 76, the CPU determines whether a difference between the sensor output value S and the initial value REF falls within a predetermined range ST. If YES in step 76, the flow advances to step 77, and if NO in step 76, the flow advances to step 78. In step 77, the initial value REF is updated to be a new sensor output value S. In step 78, the end of processing signal for resetting the flip-flop is generated. In step 80, the signal processing is ended and the power source is turned off. As described above, according to this program, the initial value REF as a reference value is initialized during initial power on (e.g., installation of the detector), and is automatically corrected thereafter during the monitoring operation to compensate for variation over time.

As has been described above, since the environmental abnormality detection apparatus of the present invention uses a microcomputer for the signal processing for determining environmental abnormalities, optimum conditions can be set, and variations in individual sensors can be minimized. In addition, power is supplied to the signal processor only for the processing time, resulting in less power consumption.

What is claimed is:

1. An environmental abnormality detection apparatus comprising:

a detection means for detecting a selected environmental abnormality;

a signal processor means connected to said detection means for processing signals therefrom for determining whether an environmental abnormality has occurred and for generating an alarm signal when the abnormality occurs, said signal processing means also including means for generating an end of processing signal; and a power source control means for intermittently supplying power to said signal processor and for stopping power supply thereto upon receipt of said end of processing signal from the signal processor.

2. An apparatus according to claim 1, wherein said power source control means comprises: an oscillator; a flip-flop having a set terminal connected to an output terminal of said oscillator; an inverter connected to a Q output terminal of said flip-flop; and a transistor having a base connected to an output terminal of said inverter, and a collector connected to said signal processor.

3. An apparatus according to claim 2 for use with a separate source, wherein said signal processing means includes a random access memory for storing data of said signal processor, said random access memory being continuously supplied with power from said separate power source.

4. An environmental abnormality detector apparatus comprising:

a detection means for detecting a selected environmental abnormality;

a signal processor means connected to said detection means for processing signals therefrom for determining whether an environmental abnormality has occurred, said signal processing means also including means for generating an end of processing signal, and having a power input;

means for generating a series of periodic pulses;

a flip-flop having a set input to which said periodic pulses are supplied, a reset input to which said end of processing signal is supplied, and a Q output; and a transistor having a control terminal connected to an output of an inverter, a first terminal connected to a source of power, and a second terminal connected to said power input of said signal processor means, said transistor supplying power to said signal processor means upon the occurrence of a pulse from said means for generating pulses which causes said flip-flop to generate a signal rendering said transistor conductive, until said signal processor means generates said end of processing signal, which causes said flip-flop to generate a signal rendering said transistor non-conductive.

* * * * *